United States Patent [19]

Chen et al.

[11] Patent Number: 5,144,062
[45] Date of Patent: Sep. 1, 1992

[54] PROCESS FOR PRODUCING METHYL FORMATE

[75] Inventors: Shien-Chang Chen, Taipei; Wan-Jy Cheng; Fu-Shen Lin, both of Kaohsiung; Fu-Juh Huang, Kaohsiung, all of Taiwan

[73] Assignee: Dairen Chemical Corporation, Taipei, Taiwan

[21] Appl. No.: 578,958

[22] Filed: Sep. 7, 1990

Related U.S. Application Data

[63] Continuation-in-part of Ser. No. 340,212, Apr. 19, 1989, abandoned.

[51] Int. Cl.$^5$ .................. C07C 67/40; C07C 69/06
[52] U.S. Cl. .................................................. 560/239
[58] Field of Search ........................................ 560/239

[56] References Cited

U.S. PATENT DOCUMENTS

| | | | |
|---|---|---|---|
| 1,400,195 | 12/1921 | Willkie | 560/239 |
| 1,857,921 | 5/1932 | Lazier | 560/239 |
| 4,126,748 | 11/1978 | Scholz | 560/239 |
| 4,220,803 | 9/1980 | Marcinkowsky et al. | 560/239 |
| 4,319,037 | 3/1982 | Yoneoka | 560/239 |

FOREIGN PATENT DOCUMENTS 3642835 6/1988 Fed. Rep. of Germany ...... 560/239

*Primary Examiner*—Vivian Garner
*Attorney, Agent, or Firm*—Michael N. Meller

[57] ABSTRACT

A process for the preparation of methyl formate by the vapor phase dehydrogenation of methanol in the presence of a catalyst composed of copper oxide, a chromium oxide and a sodium compound is described.

5 Claims, No Drawings

PROCESS FOR PRODUCING METHYL FORMATE

This is a continuation in part application of U.S. Ser. No. 340,212 filed Apr. 19, 1989 now abandoned.

BACKGROUND OF INVENTION

1. Field of the invention

This invention relates to a process for producing methyl formate by dehydrogenating methanol in the vapor phase in the presence of a catalyst of composed copper oxide and a chromium oxide and a sodium compound.

A conventional process for producing methyl formate comprises the esterification of formic acid with methanol, during which a large amount of water is also produced. In the present invention, hydrogen of high purity is produced which can be used as a chemical raw material or as a clean fuel. The selectivity of methyl formate is high and catalyst life is long.

2. Description of the prior art

Prior art processes for producing methyl formate include (a) a process wherein methanol is dehydrogenated in the presence of a catalyst containing copper and cement (U.S. Pat. No. 4,232,171); (b) a process for producing methyl formate where methanol is dehydrogenated over a catalyst produced by reducing a precursor comprising copper oxide and a spinal structure support comprising the oxides of zinc and aluminum, said precursor containing 10 to 80 percent copper. The dehydrogenation temperature is 235° C. to 350° C. (U.S. Pat. No. 4,480,122); (c) a process for producing methyl formate where methanol is dehydrogenated in the presence of a catalyst containing copper and zinc (Japanese patent 53-108916); (d) Japanese patent 54-12315 describes a catalyst containing oxides of copper, zinc and aluminum; (e) Japanese patent 56-7741 describes a catalyst containing copper, zirconium, and calcium; (f) Japanese patent 57-203034 describes a dehydrogenation which is carried out in the liquid phase and in the presence of a catalyst containing chromium.

Among the above-mentioned processes, it appears that in process (a) the conversion of the methanol and yields of methyl formate diminish significantly after running the operation for 24 hours. The process (b) says that the reaction temperatures are about 235° C. to about 350° C., which means if the temperature is below 235° C., the conversion of methanol will decrease significantly, and higher temperature results in a lower selectivity. The processes (c), (d) and (e) teach that the catalyst used is quite different from the catalyst used in the present invention. The process (f) teaches that the reaction is carried out in the liquid phase which means that an additional step of catalyst separation is necessary.

SUMMARY OF THE INVENTION

An object of the present invention is to provide a process for the production of methyl formate wherein methyl formate can be obtained in a simple step from methanol.

Another object of the present invention is to provide a process for the production of methyl formate wherein the selectivity to methyl formate is high, and without the formation of any by-product.

A further object of the present invention is to provide a process for the production of methyl formate wherein the deterioration of the catalytic activity is extremely low, so that its operation life can be extended.

The present inventors have conducted extensive research in order to develop a process for production of methyl formate by vapor phase dehydrogenation of methanol. As a result of such research, it has now been found that catalysts of the present invention, i.e., copper oxide, chromium oxide, and sodium compound have high selectivity to methyl formate. The present invention has been accomplished on the basis of the results of this research.

DETAILED DESCRIPTION OF THE INVENTION

The catalyst employed in this invention contains a copper oxide, a chromium oxide and a sodium compound.

A variety of copper compounds can be used as the copper component constituting the catalyst. Examples of the copper compounds include the hydroxide, oxides, carbonate, inorganic acid salts and organic acid salts of copper.

A variety of chromium compounds can be used as the chromium component constituting the catalyst. Examples of the chromium compounds include the oxides, inorganic acid salts and organic acid salts of chromium.

The weight ratio of copper oxide to chromium oxide is about 95/5 to 75/25, with the ratio 92/8 to 81/19 being preferred.

The sodium compound may be sodium hydroxide, sodium oxide, sodium carbonate or sodium bicarbonate.

The catalyst used in this invention can be prepared by a convenient industrial process. The preferred process is the following: The copper compound solution is added to a solution of chromium compound, the pH of the resultant solution is adjusted to form a precipitate. The precipitate is washed with water and then dried at about 70° C. To this is added a solution of the sodium compound and the wet precipitate is dried at about 70° C. The dried precipitate is baked at temperature of about 450° C. in air or nitrogen; then the baked precipitate is chemically reduced at a temperature of about 200° C. in hydrogen gas to activate it.

The dehydrogenation of methanol is carried out by contacting the catalyst with methanol in the vapor phase to produce methyl formate. The reaction temperature may be in the range of from about 140° C. to about 280° C., preferably from about 180° C. to about 240° C., and the gas space velocity of methanol may be in the range from about 50 hr$^{-1}$ to about 50,000 hr$^{-1}$, preferably from about 500 hr$^{-1}$ to about 5,000 hr$^{-1}$, and the reaction may be carried our in the range of about 1 atmosphere to about 10 atmospheres.

The catalyst used in this invention is stable for a long time and the selectivity of methanol is high. Therefore, the present invention is industrially valuable.

The present invention is further illustrated by the following examples. However, this invention should not be limited to these examples; changes and modifications within the spirit and scope of this invention can be effected.

COMPARISON EXAMPLE 1

The catalyst was prepared as described in the example of U.S. Pat. No. 4,232,171. The components were prepared in such proportion that copper oxide is 78% wt, cement is 22% wt.

A reactor having a 23.5 mm inside diameter was filled with 20 ml of the catalyst as prepared by the above procedure.

The catalyst was reduced at a temperature of 200° C. under atmospheric pressure by introducing hydrogen gas continuously at a gas hourly space velocity of 5,000 hr$^{-1}$ for 8 hours.

Methanol was then fed into the reactor at a gas hourly space velocity of 2,500 hr$^{-1}$ and maintained at the temperature of 180° C. under atmospheric pressure for at least 16 hours. The test results are shown in table 1, below.

COMPARISON EXAMPLE 2

The catalyst was prepared as described in the example of U.S. Pat. No. 4,480,122. The components were prepared in such proportion that copper oxide is 60% wt, zinc oxide is 30% wt and alumina is 10% wt.

The reaction was carried out under the same conditions as described in comparison example 1. The test results are shown in table 1, below.

COMPARISON EXAMPLE 3

The catalyst was prepared as described in the example of Japanese patent 58-163,444. The components were prepared in such proportion that copper oxide is 83% wt, zinc oxide is 4.2% wt, alumina is 8.3% wt, copper phosphate is 2.8% wt and sodium phosphate is 1.7% wt.

The reaction was carried out under the same conditions as described in comparison example 1. The test results are shown in table 1, below.

CATALYST PREPARATION PROCEDURES (1) 210 Grams copper nitrate, $Cu(NO_3)_2 \cdot 3H_2O$, was dissolved in 400 ml demineralized water, heated to 70° C.

(2) 23 Grams ammonium chromate, $(NH_4)_2 CrO_4$, was dissolved in 100 ml demineralized water, heated to 70° C.

(3) Solution (2) was added to solution (1) slowly, with good stirring.

(4) The pH value of the solution of step (3) was adjusted to 9-10 with ammonia solution.

(5) The resultant precipitate was filtered on a funnel, and washed with demineralized water.

(6) The wet precipitate was dried in an oven at a temperature of 70° C. overnight, then calcined at 450° C. for 4 hours.

(7) The powder was compressed into a cylinder 3 mm in diameter by 3 mm in height.

(8) The weight ratio of copper oxide (CuO) to chromium oxide ($Cr_2O_3$) obtained was 86/14.

A reactor having 23.5 mm diameter was filled with 20 ml of the catalyst which was prepared as in the above procedures.

The catalyst was reduced at a temperature of 200° C. under atmospheric pressure by introducing hydrogen gas at a gas hourly space velocity of 5,000 hr−1 for 8 hours.

Methanol was then fed into the reactor at a gas hourly space velocity of 2,500 hr−1 and the temperature was maintained at 180° C. under atmospheric pressure for 48 hours. The test results are shown in table 2, below.

EXAMPLE 2

The catalyst was prepared by the same procedures as described in example 1 except that copper chloride and chromium nitrate were used in place of copper nitrate and ammonium chromate in example 1. The weight ratio of copper oxide to chromium oxide obtained was 75/25.

The catalyst reduction was carried out under the same conditions as described in example 1.

The dehydration reaction was carried out under the same conditions as described in example 1 except the gas hourly space velocity was 50 hr$^{-1}$ in place of 2500 hr$^{-1}$. The test results are shown in table 2, below.

EXAMPLE 3

The catalyst was prepared by the same procedures as described in example 1 except for the variation of copper compound and chromium compound used. The resultant catalyst had a weight ratio of copper oxide to chromium oxide of 95/5.

The catalyst reduction was carried out under the same conditions as described in example 1.

The dehydrogenation reaction was carried out under the same conditions as described in example 1 except the gas hourly space velocity was 50,000 hr$^{-1}$ and 2,500 hr$^{-1}$, respectively. The test results are shown in table 2, below.

EXAMPLE 4

The catalyst was prepared by the same procedures as described in example 1 except that copper nitrate and chromium ammonium sulfate were used. The weight ratio of copper oxide to chromium oxide was 83/17.

The reduction was carried out under the same conditions as described in example 1.

The reaction was carried out under the conditions as described in example 1 except the reaction temperature was 140° C. and hourly gas space velocity was 10,000 hr$^{-1}$. The test results are shown in table 2, below.

EXAMPLE 5

The catalyst was prepared by the same procedures as described in example 1 except the copper compound was copper acetate and the chromium compound was chromium sulfate, the weight ratio of copper oxide to chromium oxide was 95/5.

The reduction and dehydration reaction were carried out under the same conditions as described in example 1 except the reaction temperature of 280° C. was used, the gas hourly space velocity was 1,000 hr$^{-1}$. The test results are shown in table 2, below.

EXAMPLE 6

The catalyst was prepared by the same procedures as described in example 1 except that copper sulfate and chromium oxide were used and the ratio of copper oxide to chromium oxide was 81/19.

The catalyst was reduced under the same conditions as described in example 1.

The dehydration reaction was carried out under the same conditions except the pressure was 10 ATM and gas hourly space velocity was 25,000 hr$^{-1}$. The test results are shown in table 2, below.

EXAMPLES 7 THROUGH 12

The purpose of these examples is to illustrate the effect of sodium on these catalysts, the advantages of which pertain: (1) promote the conversion, selectivity, and yield; and (2) prolong the catalytic cycle.

EXAMPLE 7

Catalyst preparation procedures (1) 210 Grams of copper nitrate, $Cu(NO_3)_2 \cdot 3H_2O$, were dissolved in 400 ml demineralized water, heated to 70° C.

(2) 23 Grams ammonium chromate, $(NH_4)_2CrO_4$, were dissolved in 100 ml demineralized water, heated to 70° C.

(3) Solution (2) was added to solution (1) slowly, with good stirring.

(4) The pH value of the solution of step (3) was adjusted to 9–10 with ammonia solution.

(5) The resultant precipitate was filtered on a funnel, and washed with demineralized water.

(6) The wet precipitate of step (5) was dried in an oven at a temperature of 70° C. overnight.

(7) 0.81 Grams sodium hydroxide, NaOH, was dissolved in 20 ml demineralized water.

(8) The precipitate of step (6) was impregnated with sodium hydroxide solution of step (7).

(9) The wet precipitate of step (8) was dried in an oven at a temperature of 70° C. overnight, then calcined at 450° C. for 4 hours.

(10) The powder was compressed into a cylinder 3 mm in diameter by 3 mm in height.

(11) The weight ratio of copper oxide (CuO) to chromium oxide ($Cr_2O_3$) was 86/14, the sodium content was 0.2% by weight.

A reactor having 23.5 mm diameter was filled with 20 ml of the catalyst which was prepared as the above procedures.

The catalyst was reduced at a temperature of 200° C. under atmospheric pressure by introducing hydrogen gas at a gas hourly space velocity of 5,000 $hr^{-1}$ for 8 hours.

Methanol was then fed into the reactor at a gas hourly space velocity of 2,500 $hr^{-1}$ and the temperature maintained at 180° C. under atmospheric pressure for 48 hours. The test results are shown in table 3, below.

Comparing the test results of example 1 and example 7, the differences between the catalyst with and without sodium are shown below:

(1) the conversion to methyl formate is increased from 34.6 mole % to 37.5 mole % with sodium.

(2) the selectivity is increased from 91.2 mole % to 93.1 mole % with sodium.

(3) the yield is increased from 31.6 mole % to 34.9 mole % with sodium.

(4) the catalyst cycle (the operation period for yield greater than 30 mole %) lengthened from 125 hours to 406 hours with sodium.

EXAMPLE 8

The catalyst was prepared by the same procedures as described in example 7 except that copper chloride and chromium nitrate were used in place of copper nitrate and ammonium chromate in example 7 and the sodium content was changed to 0.3% by weight, the weight ratio of copper oxide to chromium oxide was 75/25.

The catalyst reduction was carried out under the same conditions as described in example 7.

The dehydration reaction was carried out under the same conditions as described in example 7 except the gas hourly space velocity was 50 $hr^{-1}$ in place of 2,500 $hr^{-1}$. The test results are shown in table 3, below.

EXAMPLE 9

The catalyst was prepared by the same procedures as described in example 7 except the variety of copper compound and chromium compound used. The resultant catalyst had the weight ratio of copper oxide to chromium oxide 95/5.

The catalyst reduction was carried out under the same conditions as described in example 7 except the gas hourly space velocity was 50,000 $hr^{-1}$ and 2,500 $hr^{-1}$, respectively. The test results are shown in table 3, below.

EXAMPLE 10

The catalyst was prepared by the same procedure as described in example 7 except that copper nitrate and chromium ammonium sulfate were used and the sodium content was changed to 0.1% by weight. The weight ratio of copper oxide to chromium was 83/17.

The reduction was carried out under the same conditions as described in example 7.

The reaction was carried out under the conditions as described in example 7 except the reaction temperature was 140° C. and gas hourly space velocity was 10,000 $hr^{-1}$. The test results are shown in table 3, below.

EXAMPLE 11

The catalyst was prepared by the same procedures as described in example 7 except the copper compound was copper acetate and chromium compound was chromium sulfate and the sodium content was changed to 0.5% by weight, the weight ratio of copper oxide to chromium oxide was 95/5.

The reduction and dehydrogenation reactions were carried out under the same conditions as described in example 7 except the reaction temperature of 280° C. was used, the gas hourly space velocity was 1,000 $hr^{-1}$. The results are shown in table 3, below.

EXAMPLE 12

The catalyst was prepared by the same procedures as described in example 7 except the copper sulfate and chromium oxide were used and the ratio of copper oxide to chromium oxide as 80/20 and the sodium content was changed to 0.4% by weight.

The catalyst was reduced under the same conditions as described in example 7.

The dehydrogenation reaction was carried out under the same conditions except the pressure was 10 atm and gas hourly space velocity was 25,000 $hr^{-1}$. The test results are shown in table 3, below.

TABLE 1

|  | Comparison example | | |
| --- | --- | --- | --- |
|  | 1 | 2 | 3 |
| Temperature °C. | 180 | 180 | 180 |
| Pressure atm | 1 | 1 | 1 |
| GHSV $hr^{-1}$ | 2,500 | 2,500 | 2,500 |
| Conversion mole % | 16.1 | 8.5 | 17.6 |
| Selectivity mole % | 88.2 | 91.0 | 90.4 |
| Yield mole % | 14.2 | 7.7 | 15.9 |

TABLE 2

| | example | | | | | |
|---|---|---|---|---|---|---|
| | 1 | 2 | 3 | 4 | 5 | 6 |
| copper compound | copper nitrate | copper chloride | copper acetate | copper nitrate | copper acetate | copper sulfate |
| chromium compound | ammonium chromate | chromium nitrate | chromium acetate | chromium ammonium sulfate | chromium sulfate | chromium oxide |
| copper oxide/chromium oxide (wt. ratio) | 86/14 | 75/25 | 95/5 | 83/17 | 95/5 | 81/19 |
| temperature C. | 180 | 180 | 180 | 140 | 280 | 160 |
| pressure atm | 1 | 1 | 1 | 1 | 1 | 10 |
| GHSV $Hr^{-1}$ | 2500 | 50 | 50000 | 10000 | 1000 | 25000 |
| conversion mole % | 34.6 | 38 | 29.8 | 13.8 | 30.7 | 20.1 |
| selectivity mole % | 91.2 | 81.2 | 93.2 | 97.2 | 87.5 | 94.6 |
| yield mole % | 31.6 | 30.8 | 27.8 | 13.4 | 26.9 | 19.0 |

TABLE 3

| | example | | | | | |
|---|---|---|---|---|---|---|
| | 7 | 8 | 9 | 10 | 11 | 12 |
| copper compound | copper nitrate | copper chloride | copper acetate | copper nitrate | copper acetate | copper sulfate |
| chromium compound | ammonium chromate | chromium nitrate | chromium acetate | chromium ammonium sulfate | chromium sulfate | chromium oxide |
| copper oxide/chromium oxide (wt. ratio) | 86/14 | 75/25 | 95/5 | 83/17 | 95/5 | 81/19 |
| sodium content (wt. %) | 0.2 | 0.3 | 0.2 | 0.1 | 0.5 | 0.4 |
| temperature C. | 180 | 180 | 180 | 140 | 280 | 160 |
| pressure atm | 1 | 1 | 1 | 1 | 1 | 10 |
| GHSV $Hr^{-1}$ | 2500 | 50 | 50000 | 10000 | 1000 | 25000 |
| conversion mole % | 37.5 | 41.2 | 32.7 | 16.9 | 34.1 | 23.6 |
| selectivity mole % | 93.1 | 83.6 | 94.9 | 97.8 | 90.4 | 96.3 |
| yield mole % | 34.9 | 34.4 | 31.0 | 16.5 | 30.8 | 22.7 |
| *catalytic cycle (hr) with sodium | 406 | 384 | 132 | 0 | 75 | 0 |
| *catalytic cycle (hr) without sodium | 125 | 63 | 0 | 0 | 0 | 0 |

Remark
*the catalytic cycle means the operation period for yield greater than 30 mole %.

We claim:

1. A process for producing methyl formate by vapor phase dehydrogenation of methanol in the presence of a catalyst consisting essentially of copper oxide, chromium oxide, and a sodium compound wherein the weight ratio of copper oxide to chromium oxide is from 95/5 to 75/25 and the sodium content is from 0.1 to 0.5 wt. %, at a temperature of from 140° to 280° C. and at a pressure of from 1.0 to 10 atm.

2. A process as claimed in claim 1 wherein the dehydrogenation is carried out at a temperature in the range of from 180° to 240° C.

3. A process as claimed in claim 1 wherein the dehydrogenation is carried out at a gas hourly space velocity of methanol in the range of from 50 $hr^{-1}$ to 50,000 $hr^{-1}$.

4. A process as claimed in claim 1 wherein the weight ratio of copper to chromium as their oxides is in the range of from 92/8 to 80/20.

5. A process as claimed in claim 1 wherein the catalyst is calcined at about 450° C. for four hours.